United States Patent
Van Zant et al.

(10) Patent No.: US 10,604,756 B2
(45) Date of Patent: Mar. 31, 2020

(54) PROTECTION AGAINST IONIZING RADIATION AND CHEMOTHERAPY TOXICITY VIA LATEXIN REGULATION

(71) Applicant: University of Kentucky Research Foundation, Lexington, KY (US)

(72) Inventors: Gary Van Zant, Lexington, KY (US); Ying Liang, Lexington, KY (US); Yi Liu, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 14/879,577

(22) Filed: Oct. 9, 2015

(65) Prior Publication Data

US 2016/0102311 A1   Apr. 14, 2016

Related U.S. Application Data

(60) Provisional application No. 62/061,890, filed on Oct. 9, 2014.

(51) Int. Cl.
*C12N 15/113* (2010.01)
*C07K 14/81* (2006.01)
*A61K 31/713* (2006.01)

(52) U.S. Cl.
CPC .......... *C12N 15/113* (2013.01); *A61K 31/713* (2013.01); *C07K 14/81* (2013.01); *C12N 2310/11* (2013.01); *C12N 2310/12* (2013.01); *C12N 2310/14* (2013.01)

(58) Field of Classification Search
CPC .... A61K 38/00; A61K 2300/00; A61K 38/17; A61K 38/1709; A61K 31/70; A61K 31/7088; A61K 31/713; C07K 14/47; C07K 14/00; C07K 14/435; C12N 15/113
See application file for complete search history.

(56) References Cited

U.S. PATENT DOCUMENTS

| | | | | |
|---|---|---|---|---|
| 8,110,184 B2 * | 2/2012 | Van Zant | ............ | C12N 5/0647 424/93.7 |
| 9,284,530 B2 * | 3/2016 | Van Zant | ............ | C12N 5/0647 |
| 2007/0116681 A1 * | 5/2007 | Van Zant | ............ | C12N 5/0647 424/93.7 |
| 2010/0183585 A1 * | 7/2010 | Van Zant | ............... | C07K 16/18 424/130.1 |

OTHER PUBLICATIONS

Liang et al. The quantitative trait gene latexin influences the size of the hematopoietic stem cell population in mice. Nature Genet 39(2): 178-188, Jan. 14, 2007.*
Liang et al. Hematopoietic stem cell expansion by inactivation of latexin. Clin Translat Sci 7(3): 214-215, Jun. 2014.*
Liu, Yi. Latexin's rolde in regulating hematopoietic stem and progenitor cells. Theses and Dissertations-Physiology, Paper 11, 2013.*
Van Zant et al. Natural genetic diversity as a means to uncover stem cell regulatory pathways. Ann NY Acad Sci 1176: 170-177, 2009.*
Abd Elmageed et al. Clinical significance of CD146 and latexin during different stages of thryoid cancer. Mol Cell Biochem 381: 95-103, 2013.*
"Environmental Radiation", Iowa State University Environmental Health and Safety, www.ehs.iastate.edu/radiation/environmental-radiation, downloaded Oct. 11, 2017, 3 total pages.*
Li et al. Latexin expression is downregulates in human gastric carcinomas and exhibits tumor suppressor potential. BMC Cancer 11: 121, 2011 (11 total pages).*
Muthusamy et al. The hematopoietic stem cell regulatory gene latexin has tumor-suppressive properties in malignant melanoma. J Invest Dermatol 133: 1827-1833, 2013.*
Ni et al. Latexin exhibits tumor suppressor potential in hepatocellular carcinoma. Oncol Reports 31: 1364-1372, 2014.*
Sanders, C.L.L. Radiation Hormesis and the Linear-No-Threshold Assumption, Springer-Verlag Berlin Heidelberg, 2010, pp. 37-42.*
Wahl, L.E., "Environmental Radiation" Fact Sheet, Health Physics Society, Jan. 2010 (six total pages).*
Liu et al. Latexin is down-regulated in hematopoietic malignancies and restoration of expression inhibits lymphoma growth. PLOS One 7(9): E44979, 2012; 12 total pages.*
Zhang et al. Latexin and hematopoiesis. Curr Opin Hematol 25(4): 266-272, 2018.*

* cited by examiner

Primary Examiner — Bridget E Bunner
(74) Attorney, Agent, or Firm — Crowell & Moring LLP (57) ABSTRACT

The present invention relates to methods for protecting against damage caused by radiation and/or chemotherapy, and methods for treating bone marrow damage by reducing/inhibiting Latexin expression and/or Latexin activity. The methods comprise administering to a subject in need thereof a pharmaceutical composition comprising an antagonist that reduces expression and/or activity of latexin, wherein latexin is a latexin polynucleotide variant and/or a latexin polypeptide variant that binds to the antagonist.

22 Claims, 4 Drawing Sheets
Specification includes a Sequence Listing.

PROTECTION AGAINST IONIZING RADIATION AND CHEMOTHERAPY TOXICITY VIA LATEXIN REGULATION

STATEMENT OF GOVERNMENT INTEREST

This invention has been made with Government support, awarded by the National Center for Advancing Translational Sciences, National Institutes of Health, grant number KL2TR000116. The government has certain rights in the invention.

TECHNICAL FIELD

The present invention relates to methods for protecting against damage caused by radiation and/or chemotherapy by reducing/inhibiting Latexin expression and/or Latexin activity.

BACKGROUND OF THE INVENTION

Hematopoiesis is a complex process for producing multiple and distinct lineages of blood-borne cells throughout the life span of an organism. Hematopoietic stem cells ("HSCs") represent a subset of undifferentiated cells that resides predominantly in the bone marrow of adult mammals. HSCs, as a population, are capable of self-renewal by maintaining a sufficient number of HSCs within an organism's bone marrow as a reservoir of uncommitted cells that can be further differentiated into various types of new blood cells. Such newly generated blood cells emerge from the bone marrow and enter the circulatory system in order to continuously replace mature/aging circulating blood cell types. The ability of HSCs, as a population, to differentiate and to give rise to cells of multi-lineages is critical for the preservation of an organism.

In order for the maintenance of steady-state hematopoiesis, a balance must be achieved between the rate of self-generation (i.e., for maintaining a steady supply of HSCs) and the rate of differentiation (i.e., for replenishing senescent cells). Hematopoiesis occurs as a developmental continuum in that a given population of HSCs is representative of a heterogeneous mixture of cells, mainly composed of long-term HSCs ("LT-HSCs") and short-term HSCs ("ST-HSCs"). LT-HSCs are stem cells that have the capacity for self-renewal throughout the life span of an organism. However, ST-HSCs exhibit transient self-renewal properties for a limited period of time (e.g., typically less than 8 weeks in a mouse) prior to undergoing full differentiation. HSCs can differentiate into hematopoietic progenitor cells ("HPCs") that can further differentiate into clonogenic cells, or cells of a single lineage. For example, the differentiation of common lymphoid progenitors ("CLPs") can produce T lymphocytes ("T cells"), B lymphocytes ("B cells"), and natural killer cells ("NKs"). The differentiation of common myeloid progenitors ("CMPs") can generate blood cells of other lineages, including erythrocytes, macrophages, granulocytes, and platelets. The maintenance of mature blood-borne cells in the peripheral circulation is critical for various processes, including oxygen delivery and immunological protection.

Maintaining a stable supply of mature blood cells is essential for nutrient supply, pathogen defense and tumor surveillance in hematopoiesis. However, this homeostasis can be perturbed by a DNA-damaging agent such as ionizing radiation or chemotherapy. Ionizing radiation is a high-frequency radiation that has very high energy and the capacity to remove an electron from an atom. When ionizing radiation passes through a cell, its high energy causes intracellular atoms and molecules to become excited, or "ionized". This ionization can break chemical bonds, produce free radicals, and damage molecules (e.g. DNA, RNA, proteins, and lipids), which are vital in biological processes.

The blood forming-organs, reproductive organs, digestive organs, skin, bone and teeth are primary targets of radiation. Among the tissues mentioned above, the blood system is most sensitive to radiation due to its high turnover rate. In mouse model, after exposure to irradiation, blood cell numbers drops precipitously (drop stage), reaching a nadir around day 3 (nadir stage). Subsequently, the number of blood cells begins to recover and reaches to a nearly normal level around 30 days post irradiation (recovery stage).

The most critical period for a subject's survival after radiation injury is within the first two weeks. For example, if mice are exposed to 6-7Gy total body irradiation, about the $5^{th}$ or $6^{th}$ day following exposure a few of the mice may begin to appear lethargic and start to die. Daily mortality increases to a peak between the $10^{th}$ and $14^{th}$ day then gradually subsides. After the $20^{th}$ day deaths are infrequent and the surviving mice show evidence of recovery.

After exposure to ionizing radiation, radiation-induced DNA damage immediately halts cell cycle progression (cell cycle arrest). During the period of cell cycle arrest, DNA repair machinery is triggered and begins to repair the damage. If the repair is unsuccessful, the cells are removed by a programmed cell death mechanism (apoptosis). HSC apoptosis increases after radiation exposure. At the $7^{th}$ day post 6.5Gy total body irradiation, which is the time-point when the apoptotic rate reaches the peak, around 20% HSCs (Lin-Sca-1+c-Kit+cells) undergo apoptosis.

In some cells, the cell cycle arrest becomes permanent. These cells lose their proliferation capacity and become senescent. A study on human HSCs ($CD133^+$ cells) demonstrated that, even though these cells were successfully repaired, their ability to self-renew was permanently damaged. An increase in $p16^{Ink4a}$ expression on HSCs also implies the induction of premature senescence in these cells.

In some circumstances, apoptosis and senescence do not functionally remove all of the damaged cells. A small number of cells survive radiation stress with chromosome aberrations. These cells are dangerous due to their genomic instability, and have potential to result in tumorigenesis in the future.

Therefore, ionizing radiation induced-apoptosis is necessary to balance tumorigenesis prevention and organismal survival. Low levels of apoptotic activity are beneficial to tissue regeneration and may promote the restoration of hematopoiesis when cells are exposed to ionizing radiation.

SUMMARY OF THE INVENTION

A method for protecting against hematopoietic stem cell (HSC) damage caused by chemotherapy and/or radiation, in which the subject is administered a pharmaceutical composition comprising an antagonist that reduces Latexin expression and/or Latexin activity.

DETAILED DESCRIPTION OF THE INVENTION

It has been surprisingly discovered that down-regulating Latexin (Lxn) protects hematopoietic progenitor and stem cells from damage caused by ionizing radiation and/or chemotherapy and accelerates hematopoietic and immunologic recovery.

It has also been surprisingly discovered that down-regulating Lxn suppresses radiation-induced apoptosis in hematopoietic progenitor and stem cells.

It has also been surprisingly discovered that treating a subject that could potentially be exposed to radiation (e.g. a subject scheduled for radiation treatment, or a subject accidentally exposed to environmental radiation) with a pharmaceutical composition comprising an antagonist that reduces Lxn expression and/or Lxn activity protects hematopoietic progenitor and stem cells from potential damage that could be caused by the radiation and accelerates hematopoietic and immunologic recovery. The subject may be a mammal, e.g., a primate, e.g., a human, a cow, pig, dog, cat, rat or mouse.

These discoveries provide methods for protecting HSCs in subjects, e.g., human patients, undergoing radiation therapy, chemotherapy, or subjects that have been or could be exposed to radiation (environmental, medical, or otherwise).

Definitions

As used throughout the specification and the appended claims, the terms listed below have the following meanings, wherein "a" means one or more:

The terms "hematopoietic stem cells" ("HSCs") refer to a heterogeneous mixture of undifferentiated primitive stem cells, mainly composed of long-term HSCs ("LT-HSCs") and short-term HSCs ("ST-HSCs"). LT-HSCs are undifferentiated stem cells that have the capacity for self-renewal throughout the life span of an organism. ST-HSCs are undifferentiated stem cells that have the capacity for self-renewal for a limited time prior to full differentiation into a specific lineage. For example, HSCs can differentiate into hematopoietic progenitor cells ("HPCs") that can further differentiate into clonogenic cells, or cells of a single lineage, that represent a subset of a hematopoietic lineage. HSCs include non-embryonic stem cells isolated from postnatal animals, which are known as adult stem cells. HSCs are isolated from the bone marrows of mammals that are capable of differentiating into ectodermal lineages of blood cells. HSCs include undifferentiated stem cells that exhibit a distinct profile of cell surface markers, including the following combination of markers: Thy-1$^{10}$ Sca-1$^+$ Lineage$^-$ c-kit$^{+;\ or\ CD}$150$^+$CD48$^-$ Sca-1+ Lineage- c-kit+; or Thy-1$^{10}$ CD150$^+$ CD48$^-$ Sca$^-$1$^+$ Lineage$^-$ c-kit+ (Kiel et al. Cell, Vol. 121, p. 1109-1121 (2005)). HSCs that express the combination of human counterparts for these markers are preferably contemplated. The following references are herein incorporated by reference in their entirety: Cheshier et al. PNAS Vol. 96, p. 3120-3125 (1999); Eckfeldt et al. Nature, Vol. 6, p. 726-737 (2005); Wright et al. Science Vol. 94, p. 1933-1936 (2001); and Preston et al. J. Clin. Pathol. Vol. 56, p. 86-96 (2003).

The term "Latexin" ("Lxn") refers to the Lxn gene, isoforms/variants of the Lxn gene, and gene products derived from the Lxn gene, including messenger RNA and protein. The sense-strand of a human Latexin cDNA is provided as SEQ ID NO:1. A human Latexin protein sequence is provided as SEQ ID NO:2. Latexin isoforms/variants include genes containing exon sequences having at least about 70%, 75%, 80%, 85%, 90%, 95%, 96%, 97%, 98%, or 99% sequence similarity to SEQ ID NO:1; genes containing ex on sequences having at least about 70%, 75%, 80%, 85%, 90%, 95%, 96%, 97%, 98%, or 99% sequence identity to SEQ ID NO:1; those sequences encoded by genes containing exon sequences having at least about 70%, 75%, 80%, 85%, 90%, 95%, 96%, 97%, 98%, or 99% sequence similarity to SEQ ID NO:1; those sequences encoded by genes containing exon sequences having at least about 70%, 75%, 80%, 85%, 90%, 95%, 96%, 97%, 98%, or 99% sequence identity to SEQ ID NO: 1; those sequences having at least about 70%, 75%, 80%, 85%, 90%, 95%, 96%, 97%, 98%, or 99% sequence similarity to SEQ ID NO:2; and those sequences having at least about 70%, 75%, 80%, 85%, 90%, 95%, 96%, 97%, 98%, or 99% sequence identity to SEQ ID NO:2. Latexin isoforms/variants include mammalian homologs listed in Tables 1-3. Variants useful in the methods of the present invention includes variants of SEQ ID NO:1 and/or SEQ ID NO:2 as described above, and in some embodiments variants useful in the methods of the present invention include the variants of SEQ ID NO:1 or SEQ ID NO:2 excluding the carboxypeptidase inhibitor (CARIN) described in U.S. Pat. No. 5,998,373.

The term "antagonist" refers to any compound or composition that can inhibit the expression and/or the activity of Latexin and Latexin isoforms, including sequence-specific polynucleotides that can interfere with the transcription of endogenous Latexin gene; sequence-specific polynucleotides that can interfere with the translation of Latexin mRNA transcripts (e.g., siRNAs, ribozymes); sequence-specific polypeptides that can interfere with the protein stability of Latexin, the enzymatic activity of Latexin, and/or the binding activity of Latexin with respect to substrates and/or regulatory proteins; and small molecule compounds that can interfere with the protein stability of Latexin, the enzymatic activity of Latexin, and/or the binding activity of Latexin. An effective antagonist can promote HSC proliferation by at least 25%, 30%, 35%, 40%, 45%, 50%, 55%, 60%, 65%, 70%, 75%, 80%, 85%, 90%, 95%, or 100%. An effective antagonist can suppress HSC apoptosis by at least 25%, 30%, 35%, 40%, 45%, 50%, 55%, 60%, 65%, 70%, 75%, 80%, 85%, 90%, 95%, or 100%.

Protection of Radiation and/or Chemotherapy Damage

Described herein are methods for protecting against damage caused by radiation and/or chemotherapy, in which the method comprises administering to a subject in need thereof a pharmaceutical composition comprising an antagonist that reduces Latexin expression and/or Latexin activity.

The present methods enable persons of skill in the art to decrease apoptotic frequency of HSCs and/or to promote HSC proliferation within the bone marrow of patients affected by genotoxic stress, such as radiation or chemotherapy.

Subjects in need thereof include mammalian subjects that have either already been exposed to radiation at levels sufficient to damage HSCs, and/or chemotherapy, or have not yet been exposed to such levels of radiation, and/or chemotherapy. The subject in need thereof preferably has normal levels of latexin expression in their bone marrow. In one embodiment the subject in need thereof has a solid tumor and is either already receiving chemotherapy and/or radiation therapy, or is scheduled to start chemotherapy and/or radiation therapy. In another embodiment, the subject in need thereof is likely to be exposed to radiation therapy and/or chemotherapy or a chemotherapeutic agent. The present methods include providing a pharmaceutical composition prior to exposure to radiation and/or chemotherapy/chemotherapeutic agent in order to protect the HSCs from damage caused by the radiation and/or chemotherapy/chemotherapeutic agent.

Protection against damage to HSCs is indicated, e.g., by an increase in the overall survival of the subject, by protecting the cells from DNA damage caused by the chemotherapy and/or radiation, by a decrease in the frequency of HSC apoptosis, and/or by an increase in HSC proliferation within the bone marrow of the subject.

The pharmaceutical composition useful in the methods described herein comprises a therapeutically effective amount of the latexin antagonist. The pharmaceutical composition may further comprise a pharmaceutical excipient known by persons skilled in the art. Pharmaceutical formulations for effective delivery of pharmaceutical composition will vary depending on the Latexin antagonist and mode of administration. Suitable pharmaceutical excipients and carriers are known by persons skilled in the art (Remington's Pharmaceutical Sciences (1989), which is incorporated in entirety). Pharmaceutical compositions and formulations can be administered by various methods, including by injection, oral administration, inhalation, transdermal application, or rectal administration. For oral administration, suitable formulations containing a pharmaceutical compound and pharmaceutically-compatible carriers can be delivered in various forms, such as tablets or capsules, liquid solutions, suspensions, emulsions, and the like. For inhalation, suitable formulations containing a pharmaceutical compound and pharmaceutically-compatible carriers can be delivered as aerosol formulations that can be placed into pressurized propellants, such as dichlorodifluoromethane, propane, nitrogen, and the like. For parenteral administration, suitable formulations containing a pharmaceutical compound and pharmaceutically-compatible carriers can be delivered by intra-articular, intra-venous, intramuscular, intra-dermal, intra-peritoneal, and sub-cutaneous routes.

Pharmaceutical compositions suitable for use include compositions containing a latexin antagonist in a therapeutically-effective amount to achieve its intended purpose. More specifically, a therapeutically-effective amount of the latexin antagonist means an amount effective to protect HSCs from the damage caused by exposure to ionizing radiation and/or chemotherapy. Determination of the effective amounts is well within the capability of persons skilled in the art. A dose can be formulated in animal models to achieve a circulating concentration range that includes IC50 value, defined as a dose in which 50% of cells of a culture show an effect due to the test compound. Such information can be used to more accurately determine useful doses in human subjects.

Toxicity and therapeutic efficacy of latexin antagonists can be determined by standard pharmaceutical procedures utilizing cell cultures or experimental animals in order to determine a LD50 value, the dose determined to be lethal to 50% of the exposed population, and to determine a ED50 value, the dose determined to be therapeutically effective in 50% of the exposed population. A dose ratio between toxic effect and therapeutic effect is referred to as the "therapeutic index," or it can be expressed as the ratio of the LD50 value over the ED50 value. Compounds that exhibit high therapeutic indices are preferred. The data obtained from cell culture assays and animal studies can be used in formulating a range of effective dosage for human usage. Optimal dosage range includes a ED50 dose with minimal toxicity, although the dosage may vary within this range depending on a given pharmaceutical formulation and route of administration. Dosage administered to a subject should be adjusted according to the age of the subject, the weight of the subject, the manner of administration, and other circumstances unique to each subject.

Exemplary Antagonists that Inhibit the Expression and/or Activity of Latexin and Latexin Isoforms/Variants A HSC population obtained from a donor can be induced to proliferate ex vivo under in vitro conditions, or an endogenous HSC population within a patient can be induced to proliferate in situ by exposing the HSC population of interest to various antagonists that can inhibit Latexin gene expression and/or Latexin activity.

Suitable antagonists that can inhibit the expression and/or the activity of Latexin and Latexin variants include sequence-specific polynucleotides that can interfere with the transcription of endogenous Latexin gene; sequence-specific polynucleotides that can interfere with the translation of Latexin mRNA transcripts (e.g., siRNAs, ribozymes); sequence-specific polypeptides that can interfere with (a) the protein stability of Latexin, (b) the enzymatic activity of Latexin, and/or (c) the binding activity of Latexin with respect to substrates and/or regulatory proteins; antibodies that exhibit specificity for Latexin; and small molecule compounds that can interfere with the protein stability of Latexin, the enzymatic activity of Latexin, and/or the binding activity of Latexin. An effective antagonist can promote HSC proliferation by at least 25%, 30%, 35%, 40%, 45%, 50%, 55%, 60%, 65%, 70%, 75%, 80%, 85%, 90%, 95%, or 100%, preferably by 25% to 75%, more preferably 25% to 50%.

Sequence-Specific Compounds

In one embodiment, various interfering RNAs (RNAi) that are complementary to human Latexin mRNA and mammalian orthologs can be employed by persons skilled in the art to protect HSCs from the damage caused by ionizing radiation and/or chemotherapy. By introducing such RNAi compounds to a recipient subject that has been or will be exposed to ionizing radiation therapy, ionizing radiation of levels sufficient to damage HSCs, and/or chemotherapy, the silencing or inactivation effect of RNAi compounds on Latexin gene/gene products within the HSCs can protect HSCs from the damage caused by ionizing radiation and/or chemotherapy.

Because introduction of double-stranded RNA ("d5RNA") that are longer than 30 nucleotides into mammalian cells induces a sequence-nonspecific interferon response, alternative methods for delivery of interfering RNA molecules ("RNAi") may be suitable. For example, most common form of RNAi molecules are short-interfering RNAs ("siRNAs") of 21-23 base-pairs that are chemically or enzymatically synthesized, which can be introduced into mammalian host cells by various methods, including transfections. However, unlike fungi, plants, and worms that can replicate siRNAs in vivo, transfection of siRNA produces only transient gene-silencing effect in mammalian cells. As an alternative, DNA vectors encoding precursor-like forms of siRNAs may be used for stable production of siRNAs in vivo in various cells, including mammalian cells.

In another embodiment, the compounds that protect HSCs from the damage caused by ionizing radiation and/or chemotherapy comprise an oligonucleotide that can interact with endogenous messenger RNA encoded by Latexin gene or by Latexin isoforms having at least about 70%, 75%, 80%, 85%, 90%, 95%, 96%, 97%, 98%, or 99% sequence similarity to SEQ ID NO:1 (i.e., a sense-strand of human Latexin cDNA). Such RNA oligonucleotide compounds can be single-stranded or double-stranded. Suitable lengths of RNA oligonucleotides include molecules containing 15-20 nucleotides, 20-30 nucleotides, 30-50 nucleotides, 50-75 nucleotides, 75-100 nucleotides, 100-150 nucleotides, 150-200 nucleotides, and 200-300 nucleotides. In another embodiment, the antagonist of latexin that can protect HSCs from the damage caused by ionizing radiation and/or chemotherapy include an anti-sense strand that can hybridize to an endogenously produced messenger RNA, and that can inhibit the translation of the messenger RNA.

Selection of effective siRNAs useful in the methods of this invention is based on certain known rules governing optimal selection of siRNAs. For example, siRNAs containing sequence motifs, such as $AAN_{19}TT$, $NAN_{19}NN$, $NARN_{17}YNN$, and $NANN_{17}YNN$, are effective, in which N is any nucleotide, R is a purine, and Y is a pyrimidine. In addition, regions of complementary DNA should have non-repetitive sequences, and should avoid intronic sequences. Suitable siRNAs contain approximately 30-70% GC content, contain even representation of all nucleotides on the antisense strand, and do not contain stretches of single nucleotide, especially stretches of Gs. Designing suitable siRNA molecules is within the scope of persons skilled in the art. The following references are herein incorporated by reference in their entirety: Henschel et al. Nucleic Acids Research, Vol. 32: 113-120 (2004); Naito et al. Nucleic Acids Research, Vol. 32: 124-129 (2004); Dorsett et al. Vol. 3: 318-329 (2004); and Brummelkamp et al. Nature Reviews, Vol. 3: 781-789 (2003); Pusch et al. Nucleic Acid Research, 31: 6444-6449 (2003); and Chiu et al. RNA 9: 1034-1048 (2003).

Although any region of mRNA can be theoretically targeted, certain sequences that are known binding sites for mRNA-binding proteins should be avoided, including untranslated regions, such as the "5'UTR" and "3'UTR," start-codons, and exon-exon boundaries. For some mRNA targets, siRNA-directed silencing may be more effective if the mRNA targeted siRNA sequence is selected at least 50-100 nucleotides downstream of a start codon, and preferably directed towards the 3' end of a target mRNA. In addition, the conformation of an mRNA recognition site within an mRNA target is preferably RNAse-H-sensitive, and preferably not within a highly-structured RNA region. These guidelines are generally applicable since the choice of a siRNA depends on the target mRNA sequence, and persons skilled in the art would only need to synthesize several siRNAs to validate the efficiency of each. The specificity of a siRNA for a single gene can be ascertained by performing a multiple genome-sequence alignment; such as a BLAST search of the selected sequence against sequence databases, including "Unigene" libraries associated with National Center for Biotechnology Information (NCBI). Potential off-target silencing by siRNA may be minimized by choosing a siRNA sequence with maximum sequence divergence from a list of genes with partial-sequence identity to the intended mRNA target. General principles for siRNA selection are taught by the following two review articles, which are incorporated by reference (Dorsett and Tuschl, Nature Reviews Vol. 3: 318-329, (2004); Dykxhoorn et al. Nature Reviews Vol. 4: 457-467 (2003)).

Various expression vectors can be constructed to enable stable production of siRNA-like molecules in vivo. For example, RNA-pol II promoters may be operably-linked to a hairpin precursor of a siRNA sequence of interest. RNA-pol II promoters represent a broad range of promoters that enable substantial control over parameters governing RNA expression, such as inducible, constitutive, tissue-specific, or developmentally-regulated RNA expression. Alternatively, RNA-pol III promoters may be used to produce short RNA species that do not activate the interferon pathway. Suitable RNA-pol III promoters include class III promoters that lack essential transcriptional elements downstream of a transcription initiation site, such as U6 and H1 promoters, which may be operably-linked to a siRNAencoding sequence.

Long-hairpin RNAs, imperfect shRNAs, miRNAs, and siRNAs, to be used in the present methods can be designed as follows. For example, a sub-sequence of a messenger RNA encoded by Latexin gene or by Latexin isoforms having at least about 70%, 75%, 80%, 85%, 90%, 95%, 96%, 97%, 98%, or 99% sequence similarity to SEQ ID NO:1 (i.e., a sense-strand of human Latexin cDNA), can be targeted. For example, an anti-sense strand of shRNA can be designed by selecting a sub-sequence portion of a RNA sequence complementary to endogenous Latexin messenger RNA and Latexin isoforms having at least about 70% sequence similarity to SEQ ID NO: 1.

For designing siRNA, the composition and size of the loop and length of the stem of a hairpin duplex should be considered. Suitable stem lengths for efficient silencing include a broad range, including stem lengths of 19-29 nucleotides. Suitable loop lengths for efficient silencing include a broad range, including loop lengths of 4-23 nucleotides. In certain context, hairpin structures with duplexed regions that are longer than 21 nucleotides may promote effective siRNA-directed silencing, regardless of loop sequence and length.

Various gene-delivery vectors that are practiced by persons skilled in the art can be used to introduce the present expression vectors. Examples of viral vectors that may be used to infect HSC cells include: improved adenoviral vectors (Reynold et al. Nature Biotechnology 19: 838-842 (2001)); gene-deleted adenovirus-transposon vectors (Yant et al. Nature Biotechnology 20: 999-1005 (2002)); recombinant adenoviruses (Bilang-Bleuel et al. Proc. Natl. Acad. Sci. U.S.A. 94: 8818-8823 (1997)); the Moloney-murine-leukemia-virus ("Mo-MuL V") based retroviral vectors (Auten et al., Human Gene Therapy 10: 1389-99 (2003)); and poliovirus-replicon-based vectors (Bledsoe et al., Nature Biotechnology 18: 964-969 (2000)). Examples of other suitable viral vectors include: herpes virus, mumps virus, Sindbis virus, vaccinia virus, such as the canary pox virus, and lentivirus. The usage of viral vectors is well known by persons skilled in the art, and for gene therapy uses, viral infection is preferred generally. The following references are incorporated by reference in their entirety: Robbins and Ghizzani, Mol. Med. Today 1:410-417 (1995); Robin et al. Stem Cells 20:514-521 (2002); Chen et al., Immunity 19:525-533 (2003); North et al. Immunity 16: 661-672 (2002); Zhou et al., Nature Medicine 7: 1028-1034 (2001); Ivanova et al. 298: 601-604 (2002); and Santos et al. Science 298: 597-600 (2002).

In one embodiment, various oligodeoxyribonucleic acid (ODN) molecules that are complementary to endogenous messenger RNA encoded by Latexin gene or by Latexin isoforms having at least about 70%, 75%, 80%, 85%, 90%, 95%, 96%, 97%, 98%, or 99% sequence similarity to SEQ ID NO:1 (i.e., a sense-strand of human Latexin cDNA), can be employed by persons skilled in the art to protect HSCs. By introducing such oligodeoxyribonucleic acid (ODN) molecules to a recipient subject that has been or will be exposed to ionizing radiation and/or chemotherapy, the silencing or inactivation effect of RNAi compounds on Latexin gene/gene products within the HSCs can protect HSCs from the damage caused by ionizing radiation and/or chemotherapy. Suitable oligodeoxyribonucleic acid molecules ("ODNs") are short polynucleotides of approximately 20 nucleotides in length that can hybridize with pre-mRNA and mRNA to form RNA-DNA duplexes, which are degraded by ribonuclease H ("RNase H"). Such ODNs can be chemically modified to prevent the action of RNase H, to inhibit translation of mRNA by steric hindrance, to inhibit splicing of pre-mRNAs, and to inhibit transcription by the formation of triple helices. Kurreck, J. et al., Eur. J. Biochem., 270:1628-1644 (2003); Baker et al., J. Biol. Chem., 272:11994-2000 (1997); Lu, Q. L. et al, Nature Med., 9:1009-1014 (2003); and Uil, et al., Nucleic Acids Res., 31:6064-6078 (2003) are incorporated by reference in their entirety.

In one embodiment, various ribozymes containing sequences that are complementary to endogenous messenger RNA encoded by Latexin gene or by Latexin isoforms having at least about 70%, 75%, 80%, 85%, 90%, 95%, 96%, 97%, 98%, or 99% sequence similarity to SEQ ID NO: 1 (i.e., a sense-strand of human Latexin cDNA), can be employed by persons skilled in the art in order to reduce Latexin expression and/or Latexin activity that results in the protection of HSCs from the damage caused by ionizing radiation and/or chemotherapy. Ribozymes, including the "hammer-head" ribozyme, are RNA molecules that bind target mRNA by assuming a unique secondary structure when hybridized to target mRNA, which enables catalytic hydrolysis of a phosphodiester bond within in the backbone of target mRNA. Efficient cleavage by a ribozyme requires the presence of divalent ions, such as magnesium, and is also dependent on target RNA structure, and relative proximity between ribozyme and target molecule. RNA localization signals or RNA chaperones may be used so that low concentrations of ribozymes are sufficiently effective in silencing Latexin and Latexin isoforms. Ribozymes can be chemically synthesized in vitro, and can be transcribed from expression vectors in vivo. Methods for ribozyme construction and utilization are known by persons skilled in the art. Doudna and Cech, Nature, 418:222-228 (2002); Kuwahara et al. J. Biochem., 132:149-155 (2002); Michienzi and Rossi, Methods Enzymol. 341:581-596 (2001); and Good et al. Gene Ther. 4:45-54, (1997) are herein incorporated by reference.

In another embodiment, suitable antagonists include small molecules that can bind polypeptides having at least about 70%, 75%, 80%, 85%, 90%, 95%, 96%, 97%, 98%, or 99% sequence similarity to SEQ ID NO:2, that can inhibit the activity of the bound polypeptide, and that can promote the proliferation of HSCs and/or suppress the apoptosis of HSCs. In addition, small molecules that can interact with genomic DNA containing exons having at least about 70%, 75%, 80%, 85%, 90%, 95%, 96%, 97%, 98%, or 99% sequence similarity to SEQ ID NO:1 (i.e., a sense-strand of human Latexin cDNA) can be employed. In addition, compounds that can interact with RNA transcripts encoded by a gene, in which the exon sequences have at least about 70%, 75%, 80%, 85%, 90%, 95%, 96%, 97%, 98%, or 99% sequence similarity to SEQ ID NO:1 (i.e., a sense-strand of human Latexin cDNA) can be employed. Various compounds that can inhibit the expression and/or activity of Latexin or Latexin isoforms can be either naturally-occurring or synthetically-produced. Large combinatorial libraries of chemical/biological compounds can be generated by various chemical and biological synthesis methods known in the art. Such combinatorial chemical libraries include: small organic molecule libraries (benzodiazepines, Baum C&EN, January 18, page 33 (1993)); Chen et al. J. Amer. Chem. Soc. 116:2661 (1994)), such as isoprenoids (U.S. Pat. No. 5,569, 588), thiazolidinones and metathiazanones (U.S. Pat. No. 5,549,974), pyrrolidines (U.S. Pat. Nos. 5,525,735 and 5,519,134), morpholino compounds (U.S. Pat. No. 5,506, 337), and benzodiazepines (U.S. Pat. No. 5,288,514), oligocarbamates (Cho et al. Science 261:1303 (1993)), and peptidyl phosphonates (Campbell et al., J. Org. Chem. 59:658 (1994)). Exemplary combinatorial libraries include: various peptide libraries (U.S. Pat. No. 5,010,175; Furka, Int. J. Pept. Prot. Res. 37:487-493 (1991); Houghton et al., Nature 354:84-88 (1991)); peptoid libraries (PCT Publication No. WO 91/19735); encoded peptides (PCT Publication No. WO 93/20242); random bio-oligomers (PCT Publication No. WO 92/00091); benzodiazepines (U.S. Pat. No. 5,288,514); diversomers such as hydantoins, benzodiazepines and dipeptides (Hobbs et al., Proc. Nat. Acad. Sci. USA 90:6909-6913 (1993)); vinylogous polypeptides (Hagihara et al., J. Amer. Chem. Soc. 114:6568 (1992)); nonpeptidal peptidomimetics with glucose scaffolding (Hirschmann et al. J. Amer. Chem. Soc. 114:9217-9218 (1992)); various nucleic-acid libraries; various peptide-nucleic acid libraries (U.S. Pat. No. 5,539,083); various carbohydrate libraries (Liang et al., Science, 274:1520-1522 (1996); U.S. Pat. No. 5,593,853)); and various antibody libraries (Vaughn et al., Nature Biotechnology, 14(3):309-314 (1996)).

Targeting Functionally-Related Isoforms of Latexin

The present methods and compositions can be employed for targeting variants of Latexin that have similar properties/ activities within HSCs of many types of mammalian subjects. Functionally-related isoforms of Latexin can be identified by searching various genomic databases and conducting multi-genome-wide sequence alignments in order to identify homologous sequences of interest. Related orthologous sequences can be identified by searching composite genomic databases. The breath of a database search is limited by the scope of representative model organisms for which sequence data is available.

Homology can be determined by various routine methods, including alignments of open-reading-frames ("ORFs") contained in private and/or public databases. Any suitable mathematical algorithm may be used to determine percent identities and percent similarities between any two sequences being compared. For example, nucleic acid and protein sequences of the present invention can be used as a "query sequence" to perform a search against sequences deposited within various public databases to identity other family members or evolutionarily-related sequences. Genomic sequences for various organisms are currently available, including fungi, such as the budding yeast, or *Saccharomyces cerevisiae*; invertebrates, such as *Caenorhabditis elegans* and *Drosophila melangaster*; and mammals, such as the mouse, rat, and human. Exemplary databases for identifying orthologs of interest include Genebank, Swiss Protein, EMBL, and National Center for Biotechnology Information ("NCBI"), and many others known in the art. These databases enable a user to set various parameters for a hypothetical search according to the user's preference, or to utilize default settings. Tables 1-3, provided below, list the accession numbers and gene identification numbers for exemplary mammalian orthologs. Suitable Latexin variants that may be targeted for suppression or inhibition includes e.g, the variants of SEQ ID NO: 1 or SEQ ID NO: 2 described herein. In another embodiment, suitable Latexin variants that may be targeted for suppression or inhibition include variants of SEQ ID NO: 1 or SEQ ID NO: 2 other than the carboxypeptidase inhibitor (CARIN) described in U.S. Pat. No. 5,998,373.

TABLE 1

Gene Bank Accession Number for Exemplary Mouse, Human, and Rat Latexin mRNA.

| Organism | Accession Number | Gene IDS |
|---|---|---|
| *Mus musulus* (Mouse) | NM-016753 | 31980631 |
| *Rattus norvegicus* (Rat) | NM-031655 | 14269567 |
| *Homo Sapiens* (Human) | NM-020169 | 21359932 |

TABLE 2

Gene Bank Accession Number for Exemplary Mouse, Human, and Rat Latexin Protein.

| Organism | Accession Number | Gene IDS |
|---|---|---|
| *Mus musulus* (Mouse) | NP-058033 | 31980632 |
| *Rattus norvegicus* (Rat) | NP-113843 | 14269568 |
| *Homo Sapiens* (Human) | NP-064554 | 21359933 |

TABLE 3

Mammalian Homologs for Latexin.

| Organism | Accession Number | Gene IDS | Percentage Identity | Gene Information |
|---|---|---|---|---|
| *Mus musulus* (Mouse) | AK032170.1 | 26327996 | 99.91 | *Mus musulus* adult male olfactory brain cDNA, RIKEN full-length enriched library, clone: 6430407E02 product: Latexin, full insert sequence |
| *Mus musulus* (Mouse) | AK149981.1 | 74211713 | 100.00 | *Mus musulus* bone marrow macrophage cDNA, RIKEN full-length enriched library, clone: G530111019 product: Latexin, full insert sequence |
| *Mus musulus* (Mouse) | D88769.1 | 1669620 | 99.50 | *Mus musulus* mRNA for Latexin, complete cds |
| *Mus musulus* (Mouse) | AC124190.4 | 23499687 | 100.00 | *Mus musulus* BAC clone RP23-267M9 from 3, complete sequence |
| *Mus musulus* (Mouse) | AC124190.4 | 23499687 | 100.00 | |
| *Mus musulus* (Mouse) | AC124190.4 | 23499687 | 100.00 | |
| *Mus musulus* (Mouse) | AC124190.4 | 23499687 | 100.00 | |
| *Mus musulus* (Mouse) | AC124190.4 | 23499687 | 100.00 | |
| *Mus musulus* (Mouse) | AC124190.4 | 23499687 | 100.00 | |
| *Mus musulus* (Mouse) | AK018305.1 | 12857946 | 99.58 | *Mus musulus* 10 days neonate cerebellum cDNA, RIKEN full-length enriched library, clone: 6530401A10 product: Latexin, full insert sequence |
| *Mus musulus* (Mouse) | AK198791.1 | 56022968 | 100.00 | *Mus musulus* cDNA, clone: Y1G0129D08, strand: minus, reference: ENSEMBL: Mouse-Transcript-ENST: ENSMUST00000058981, based on BLAT search |

TABLE 3-continued

Mammalian Homologs for Latexin.

| Organism | Accession Number | Gene IDS | Percentage Identity | Gene Information |
|---|---|---|---|---|
| Mus musulus (Mouse) | AK187030.1 | 56011207 | 99.52 | Mus musulus cDNA, clone: YOG0139J09, strand: minus, reference: ENSEMBL: Mouse-Transcript-ENST: ENSMUST00000058981, based on BLAT search |
| Rattus norvegicus (Rat) | Y18435.2 | 6066618 | 94.33 | Rattus norvegicus Latexin gene, exons 1 to 6 |
| Rattus norvegicus (Rat) | Y18435.2 | 6066618 | 96.92 | |

Assays

Various assays measure the number and functionality of HSCs and their progeny. These assays include in vitro phenotyping assays, in vitro clonogenic assays, and in vivo transplantation assays.

Flow cytometry reveals important information on the phenotypes of different hematopoietic cell subsets. Combining fluorescently labeled antibodies against cell surface receptors with flow cytometric analysis allows for the identification and isolation of progenitor and stem cells. Generally, there is a good correlation between the phenotype and in vivo reconstitution potential of HSCs; under stress conditions (aging, chemo/radio therapy or transplantation), phenotypic isolation strategies vary in their efficiency in selecting HSCs.

The colony-forming unit (CFU) assay is an in vitro assay widely used to detect and quantify hematopoietic progenitor cells. In this assay, BM, spleen or peripheral blood cells are mixed with methylcellulose-based medium supplied with a combination of cytokines, and cultured for one or two weeks. Progenitor cells of different lineages form colonies which have distinct morphologies. In this assay, each colony is counted and characterized by lineage according to their morphologies. Thus, it offers insight into the lineage specificity of cells, rather than assessing the functional activity of primitive, pluripotent HSCs.

The cobblestone-area forming cell (CAFC) assay is an in vitro limiting-dilution assay used to determine the frequency of hematopoietic cell subsets in a developmental hierarchy. A stromal cell layer (e.g. FBMD-1 cells) is pre-seeded and cultured in 96-well plates, and allows for in vitro long-term culturing of stem and progenitor cell. After the stromal cells reach confluency, bone marrow cells are plated on top of them. The primitive HPCs (hematopoietic progenitor cells) and HSCs will form the colony underneath the stromal cell layer. The colonies are monitored and counted under the microscope weekly for 5 weeks. The later the cells are in forming the colony, the more primitive the cells are. That is, cells forming colonies at early time-points (day 7, 14 and 21) are different stages of HPCs, and those forming colonies at day 28 and 35 are HSCs. CAFC day 35 cells are commonly used to determine primitive HSCs. CAFC assay can be used to determine the adhesion capacity of HSCs to stromal cells. In this assay, hematopoietic cells are plated onto a stromal layer and the hematopoietic cells and stromal cells are allowed to interact for 2-4 hours. The non-adherent cells are then washed away, leaving the adherent cells in culture. These adherent cells will form cobblestone-areas at later time points. The adhesion assay generally measures the adhesive properties of hematopoietic cells and studies the interaction between hematopoietic cells and stromal cells. The CAFC assay is a reliable approach for measuring the frequency and clonogenic function of hematopoietic progenitor and stem cells.

EXAMPLES

Animals

Young C57BL/6 (B6) mice (8-16 weeks) were purchased from The Jackson Laboratories (Bar Harbor, Me.). Latexin constitutive knockout mice were generated by Taconic/Artemis (Germantown, N.Y.) and used at a young age (8-16 weeks). Male animals were used in this study. All animals were housed in the animal facilities of the University of Kentucky under pathogen-free conditions according to NIH-mandated guidelines for animal welfare and were given food and water ad libitum. Lxn constitutive knock-out mice were used as a model and they were treated with ionizing radiation. The Lxn deficient mouse model was generated by Taconic/armetis under contract let by the inventors. The salient alteration was a deletion of Lxn exons 2-4 resulting in a complete knockout of LXN synthesis.

Ionizing Radiation

The mice and cells were exposed to various doses of radiation (6.5 Gy, 8 Gy, 9 Gy and split doses of 12 Gy) in a 137 Cs gamma irradiatior (J. L. Shepherd and Associates, Glendale, Ga.) at a dose rate of 153 rad/min.

Peripheral Blood Cell Counts

Animals were anesthetized with isoflurane (Butler Animal Health Supply, Dublin, Ohio). Peripheral blood was collected from retro-orbital venous plexus into EDTA-coated microtainer tubes (Becton, Dickinson and Company, Franklin Lakes, N.J.). Circulating leukocytes, erythrocytes and platelets were counted by analyzing 20 µL of blood using a Hemavet 950 (Drew Scientific, Dallas, Tex.).

Hematopoietic Cell Identification and Isolation

Bone marrow cells were flushed from the femora and tibiae using a 1 ml syringe and 22G needle into Hanks balanced salt solution (HBSS) with 2% fetal bovine serum (FBS) (Gibco, Grand Island, N.Y.). Progenitor cells were discriminated from stem cells by the lack of cell surface antigens characteristic of cells committed to individual lineages. Antibodies against these antigens included CD5 and CD8a, B220, Mac-1, Gr-1, and Ter119 were biotinylated. Strepavidin secondary antibody was used to detect lineage negative cells. To further purify primitive stem cells, the stem cell markers Sca-1 and c-Kit were incorporated into the staining procedure. Dead cells were excluded by propidium iodide (PI) that stains exposed double-strand DNA. All monoclonal antibodies were purchased from eBioscience (San Diego, Calif.), Biolegend (San Diego, Calif.), or BD Pharmingen (San Jose, Calif.).

Cell Analysis and Sorting

Bone marrow cells were analyzed and sorted on a BD FacsAria II flow cytometer (Becton Dickinson, Franklin Lakes, N.J.). Cells were sorted into phosphate buffered saline (PBS) with 0.5% FBS for further use. Flow cytometry data was analyzed using FlowJo software (Tree star, Ashland, Oreg.).

Apoptosis Analysis

Bone marrow cells were prepared and stained as described above. The fluorochrome-conjugated apoptotic marker Annexin V along with Propidium Iodide (PI) (both from BD Pharmingen) were used to identify apoptotic cells (PI−/Annexin V+). Stained cells from Lxn−/− animals and B6 animals were analyzed by flow cytometer.

Colony Forming Cell (CFC) Assay

Methylcellulose-based culture media (MethoCult) was purchased from Stem Cell Technologies, Vancouver, Canada and contained the following cytokines: stem cell factor (SCF), IL-3 and IL-6. For this assay, $5\times10^4$ whole BM cells in 100 μL HBSS were thoroughly admixed with 1 mL complete MethoCult media, plated into petri-dishes, and incubated at 37° C. Individual wells of duplicates were counted on day 10 to quantify lineage specific colonies.

Example 1

Lxn Function in Response to Hematopoietic Stress-induced Apoptosis

Figure 1A:
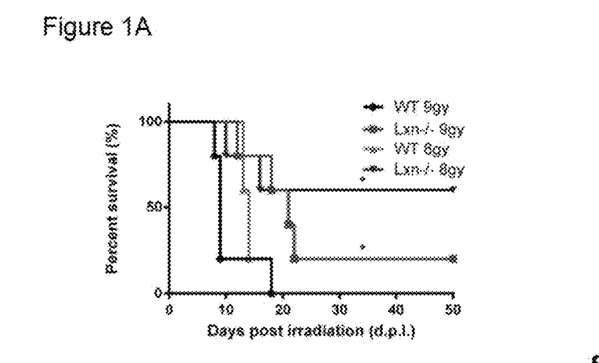
FIGS. 1A and 1B illustrate the Kaplan-Meier survival curves of mice exposed to lethal total body irradiation and the Kaplan-Meier survival curves of mice exposed to clinically relevant total body irradiation.

The effects of loss of Lxn in BM cell radiation resistance were studied first. Total body irradiation (TBI) was administered to Lxn−/− mice and to B6 control mice. Various dosages of gamma radiation including lethal doses of 8 Gy and 9 Gy were tested, as well as clinically relevant split doses totaling 12 Gy. The survival rate for each treatment was then tested. All of the lethally irradiated B6 animals died within 20 days after receiving a single 8 or 9 Gy dose (FIG. 1A). Surprisingly, the survival rate of Lxn−/− mice was significantly greater. As shown in FIG. 1A, 60% of the Lxn−/− mice survived the 8 Gy dose of irradiation and 20% of Lxn−/− mice survived the 9 Gy dose.

Figure 1B:
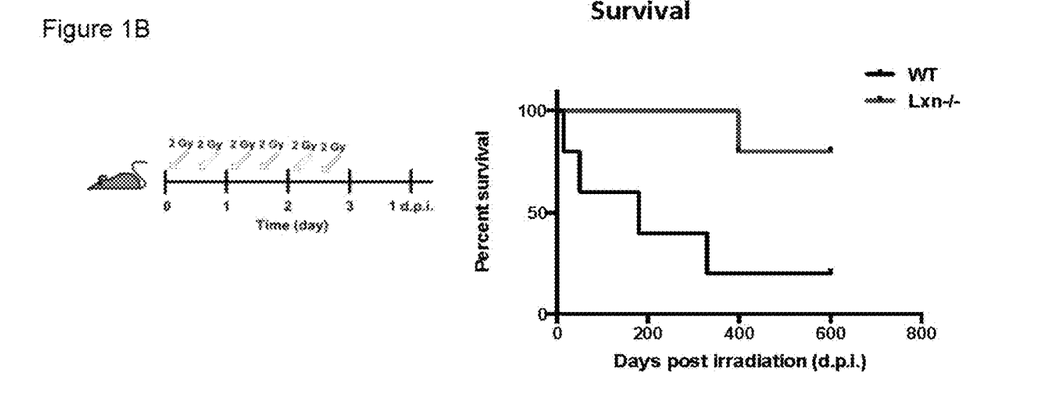

To further characterize the radio-protective effect and study its implication in medical treatment, two experimental groups were irradiated with 12 Gy TBI using a fractionated schedule of 2 Gy every 12 hours. 80% of Lxn−/− mice (4 out 5) survived over 600 days whereas only 20% of WT control mice (1 out 5) survived. The difference is significant ($p<0.05$). (FIG. 1B)

Example 2

HSC and HPC Recovery after Radiation Exposure

Figure 2A:
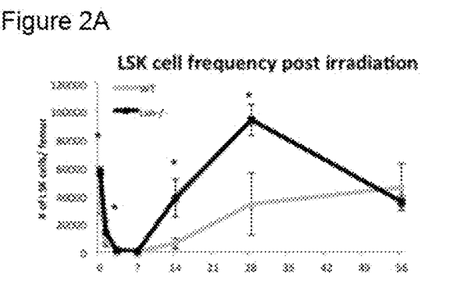
FIGS. 2A-2D illustrate the numbers of surviving LSK cell in one femur compared between B6 and Lxn−/− mice that had been irradiated with a sub-lethal dose of irradiation (6.5 Gy), flow cytometric analysis showing expanded LSK, LK, and LS cell populations at day 14 post-irradiation for both Lxn−/− and B6 mice, the frequencies of hematopoietic stem and progenitor cells as determined by an in vitro colony forming cell assay, and the numbers of surviving bone marrow cells in one femur compared between B6 and Lxn−/− mice that had been irradiated with a sub-lethal dose of radiation.

A single dose of 6.5 Gy TBI (sub-lethal dose) was administered to both experimental groups (Lxn−/− mice and wild-type B6 mice). The recovery of HSPC post irradiation was determined by both flow cytometer (which counts phenotypic HSPC) and in vitro colony-forming unit (CFU) assay (which measures functional HSPC) in a time dependent manner. At each time point, BM cells were harvested, BM cellularity was analyzed, and the size of the surviving LSK cell population in both groups was measured. The number of phenotypic HSPCs (LSK cells) in Lxn−/− mice was significant greater than B6 mice before irradiation and 3 days after exposure to irradiation (FIG. 2A). LSK cell counts dropped dramatically at day 7 in both experiment groups. However, the HSC recovery rate was accelerated in Lxn−/− mice.

Figure 2B:
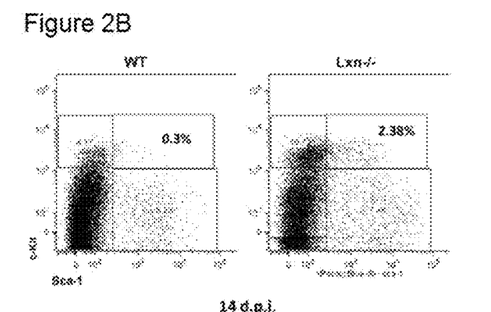

The number of LSK cells compartment increased approximately 6-fold at day 14 and 3-fold at day 21 in Lxn−/− mice (FIGS. 2A and B). The numbers of LK (Lin−/c-Kit+/Sca-1−) and LS (Lin−/c-Kit−/Sca-1+) cells were also increased at day 14, though not to the same extent of LSK cells. These data indicate that deletion of Lxn selectively protects primitive cells more so than differentiated cells (FIG. 2B).

In flow cytometric analysis, phenotypic markers were used to quantify HSPC numbers. To further identify the numbers of functional HSPCs, CFU assays were performed with $5\times10^4$ whole BM cells from 6.5 Gy sub-lethally irradiated animals. The pattern of HSPC recovery in Lxn−/− mice is similar to that pattern observed when using phenotypic markers.

Figure 2C:
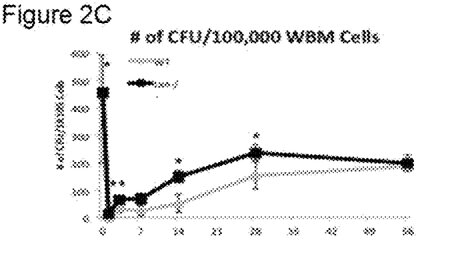

Lxn−/− whole BM cells from mice at day 0, 1, 3, 14 and 28 post irradiation formed significantly more colonies, which indicated an accelerated recovery rate compared to B6 cells (FIG. 2C). This observation supported previous LSK cell population frequency results.

Figure 2D:
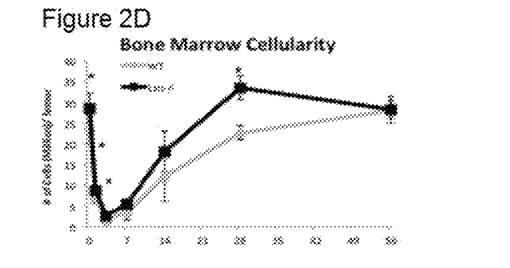

A similar trend in BM cell recovery was also observed. The numbers of surviving whole BM cells were significantly diminished (24~28 million cells per femur to less than 3 million cells per femur) shortly after irradiation (day 3), and subsequently stable returned back to normal levels by day 28 in Lxn−/− mice (FIG. 2D). Lxn−/− BM cells showed an accelerated recovery rate over B6 BM cells at day 7, 14 and 28 (FIG. 2D), in accordance with increased tempo in recovery of HSPCs (FIG. 2A).

Example 3

Hematologic and Immune Recovery

Because radiation-induced hematological failure and immune failure are the primary causes of low survival after high dose radiation exposure, hematologic and immune recovery in a time dependent manner following radiation exposure were examined.

Wild type B6 and Lxn−/− animals were exposed to a sub-lethal (6.5 Gy) dose of radiation to trigger reversible hematopoietic injury, and the rate of recovery of blood cells was monitored.

Figure 3A:
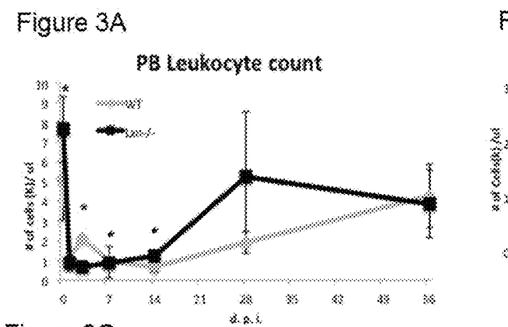
FIGS. 3A-3E illustrate the counts of total leukocytes, the counts of total neutrophils, the counts of total lymphocytes, the counts of total platelets, and differentiated lineage cells as measured by flow cytometer using lineage-specific antibodies (Gr-1, Mac-1, B220 and Thy-1) of B6 and Lxn−/− mice that had been irradiated with a sub-lethal dose of radiation.

As demonstrated in FIG. 3A, loss of Lxn significantly accelerated the recovery of total leukocytes in blood. Untreated Lxn−/− mice have ~30% more leukocytes than their wild type counterparts (FIG. 3A).

Figure 3B:
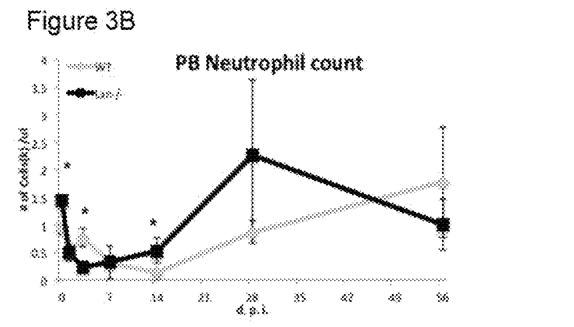
Figure 3C:
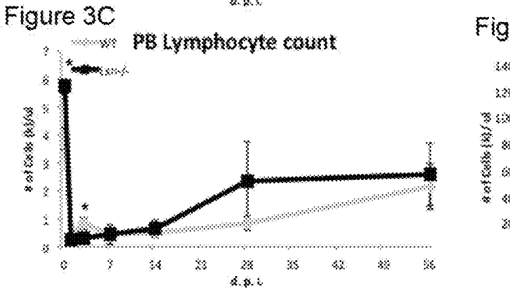

Leukocytes in both strains dropped to approximately 1,000 cells/μL in peripheral blood one day after irradiation. The number of Lxn−/− leukocytes rapidly recovered at day 7 and remained significantly greater than B6 (approximately 100% more) up to day 14. The counts of neutrophils (FIG. 3B) and lymphocytes (FIGS. 3B and 3C) had similar recovery patterns as the total leukocytes. Lxn−/− mice showed a faster recovery over the period from day 7 to 28 compared to B6 animals.

Figure 3D:
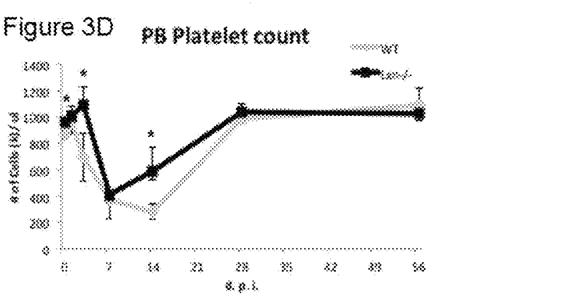

The level of neutrophil counts in both groups overshot normal levels, whereas lymphocytes never fully recovered. Platelet (FIG. 3D) counts in both groups recovered to normal by day 28. The number of Lxn−/− platelets was significantly greater than B6 platelets 3-7 after irradiation.

Collectively, a significant recovery advantage was observed at multiple time points in both hematologic and immune systems in PB, possibly resulting from accelerated recovery in HSPCs in BM.

Figure 3E:
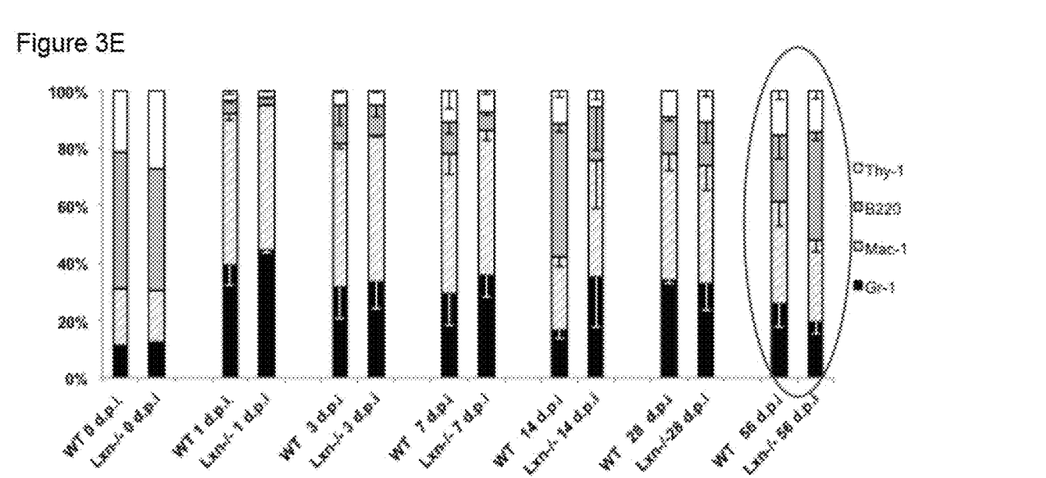

The lineage distribution of mature blood cells between granulocyte, monocyte, T-cell and B-cell lymphocytes using various lineage markers were also studied. The gamma irradiation caused immediate lympho- and myelo-ablation at day 1 and an altered lineage distribution that favored the myeloid lineage (FIG. 3E). The lymphoid lineage started to gradually recover 3 days after radiation.

The distribution of B lymphocytes in Lxn−/− mice recovered to near normal (50%), but B6 B lymphocytes never fully recovered (30%) (FIG. 3E).

In sum, the recoveries of total leukocyte, platelet, granulocyte and lymphocyte subsets were significantly accelerated in Lxn−/− mice following ionizing radiation. Further, Lxn−/− cells favor B cell lineage production in long-term reconstitution.

Example 4

Apoptotic Frequency

Figure 4A:
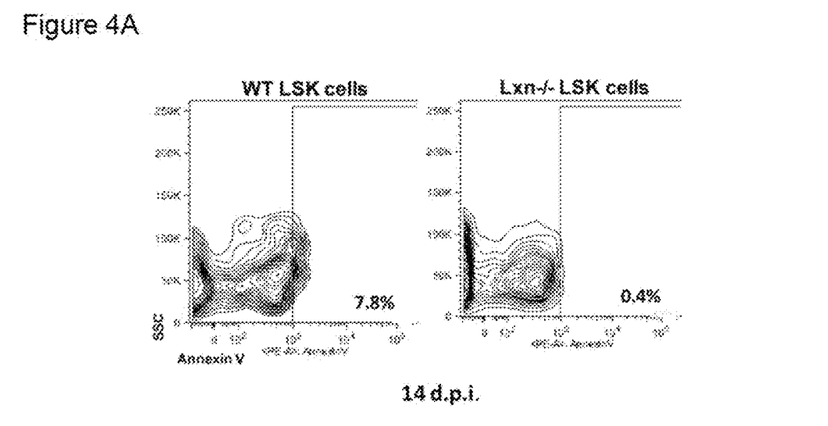
FIGS. 4A-4C illustrate the flow cytometric analysis of apoptotic cells on day 14 post-irradiation using Annexin-V and DNA dye staining, analysis of apoptotic rate dynamics (over 56 days post-irradiation) in LSK population, and the apoptotic frequency of LSK, LK, LS and LIN− sub-populations in day 14 post-irradiation of B6 and Lxn−/− mice that had been irradiated with a sub-lethal dose of radiation.
Figure 4B:
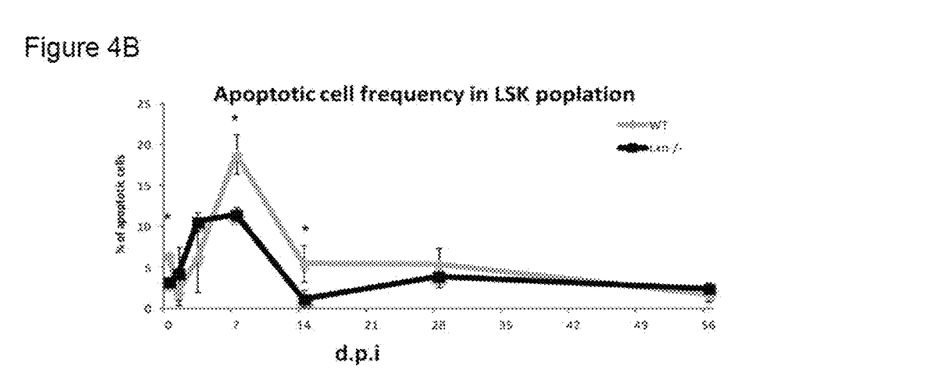
Figure 4C:
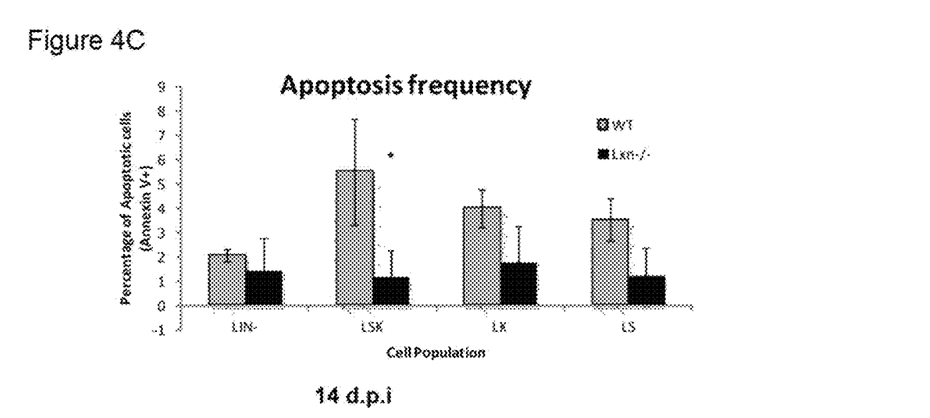

Apoptotic frequency was directly examined using Annexin V staining. The percentage of apoptotic LSK cells was significantly lower in Lxn−/− mice after 6.5 Gy sublethal irradiation (FIG. 4A). During homeostasis, apoptotic cell frequency is inherently significantly lower in Lxn−/− LSK cells (day 0 in FIG. 4A). This low apoptotic frequency was sustained from day 7 to day 28 after irradiation. On day 14 the percentage of apoptotic LSK cells was 5-fold lower in Lxn−/− mice compared to B6 mice (FIGS. 4A, 4B and 4C). Notably, the percentage of apoptotic cells in Lin−, LK and LS subpopulations diminished along with Lxn ablation on day 14, but did not reach statistical significance (FIG. 4C). The apoptotic frequency was significantly reduced only in LSK cells, indicating that loss of Lxn selectively affected the apoptotic rate in primitive BM cells.

It will be appreciated that, although specific embodiments of the invention have been described herein for purposes of illustration, various modifications may be made without departing from the spirit and the scope of the invention. Accordingly, the invention is not limited except as by the appended claims.

The invention claimed is:

1. A method for protecting against hematopoietic stem cell (HSC) damage caused by chemotherapy and/or radiation, the method comprising:
   administering to a subject in need thereof a pharmaceutical composition comprising an siRNA that reduces expression and/or activity of latexin,
   wherein latexin is a latexin polynucleotide variant that binds to the siRNA,
   wherein the latexin polynucleotide variant has at least 95% sequence identity to SEQ ID NO: 1, and
   wherein the latexin polynucleotide encodes a latexin polypeptide variant that has at least 95% sequence identity to SEQ ID NO: 2, and
   wherein the subject in need thereof has a solid tumor and is scheduled to start chemotherapy and/or radiation therapy.

2. The method of claim 1, wherein the pharmaceutical composition increases overall survival of the subject.

3. The method of claim 1, wherein the pharmaceutical composition protects the HSCs from DNA damage.

4. The method of claim 1, wherein the pharmaceutical composition decreases the frequency of HSC apoptosis.

5. The method of claim 1, wherein the pharmaceutical composition promotes HSC proliferation by at least 25%.

6. The method of claim 1, wherein the damage is caused to the bone marrow.

7. A method for protecting against hematopoietic stem cell (HSC) damage caused by chemotherapy and/or radiation, the method comprising:
   administering to a subject in need thereof a pharmaceutical composition comprising an siRNA that reduces expression and/or activity of latexin,
   wherein latexin is a latexin polynucleotide variant that binds to the siRNA,
   wherein the latexin polynucleotide variant has at least 95% sequence identity to SEQ ID NO: 1, and
   wherein the latexin polynucleotide encodes a latexin polypeptide variant that has at least 95% sequence identity to SEQ ID NO: 2, and
   wherein the subject in need thereof has a solid tumor and is already receiving chemotherapy and/or radiation therapy.

8. The method of claim 7, wherein the pharmaceutical composition increases overall survival of the subject.

9. The method of claim 7, wherein the pharmaceutical composition protects the HSCs from DNA damage.

10. The method of claim 7, wherein the pharmaceutical composition decreases the frequency of HSC apoptosis.

11. The method of claim 7, wherein the pharmaceutical composition promotes HSC proliferation by at least 25%.

12. The method of claim 7, wherein the damage is caused to the bone marrow.

13. The method of claim 1, A method for protecting against hematopoietic stem cell (HSC) damage caused by chemotherapy and/or radiation, the method comprising:
administering to a subject in need thereof a pharmaceutical composition comprising an siRNA that reduces expression and/or activity of latexin,
wherein latexin is a latexin polynucleotide variant that binds to the siRNA,
wherein the latexin polynucleotide variant has at least 95% sequence identity to SEQ ID NO: 1, and
wherein the latexin polynucleotide encodes a latexin polypeptide variant that has at least 95% sequence identity to SEQ ID NO: 2, and
wherein the subject in need thereof is selected from the group consisting of a subject receiving chemotherapy and/or radiation therapy and a subject scheduled to start chemotherapy and/or radiation therapy, and
wherein the subject in need thereof has normal levels of latexin expression in his or her bone marrow.

14. The method of claim 13, wherein the pharmaceutical composition increases overall survival of the subject.

15. The method of claim 13, wherein the pharmaceutical composition protects the HSCs from DNA damage.

16. The method of claim 13, wherein the pharmaceutical composition decreases the frequency of HSC apoptosis.

17. The method of claim 13, wherein the pharmaceutical composition promotes HSC proliferation by at least 25%.

18. A method for treating bone marrow damage, the method comprising:
administering to a patient in need thereof a pharmaceutical composition comprising an siRNA that reduces expression and/or activity of latexin,
wherein latexin is a latexin polynucleotide variant that binds to the siRNA,
wherein the latexin polynucleotide variant has at least 95% sequence identity to SEQ ID NO: 1, and
wherein the latexin polynucleotide encodes a latexin polypeptide variant that has at least 95% sequence identity to SEQ ID NO: 2, and
wherein the subject in need thereof is selected from the group consisting of a subject receiving chemotherapy and/or radiation therapy and a subject scheduled to start chemotherapy and/or radiation therapy, and
wherein the subject in need thereof has a solid tumor and wherein the bone marrow damage is caused by chemotherapy and/or radiation therapy.

19. The method of claim 18, wherein the pharmaceutical composition decreases apoptotic frequency of hematopoietic stem cells (HSCs).

20. The method of claim 18, wherein the pharmaceutical composition promotes HSC proliferation.

21. The method of claim 20, wherein the pharmaceutical composition promotes HSC proliferation by at least 25%.

22. The method of claim 18, wherein the subject in need thereof is already receiving chemotherapy and/or radiation therapy.

* * * * *

SEQUENCE LISTING

```
<160> NUMBER OF SEQ ID NOS: 2

<210> SEQ ID NO 1
<211> LENGTH: 1113
<212> TYPE: DNA
<213> ORGANISM: human

<400> SEQUENCE: 1
agaagcagtc agcccagggc tctcggatgc agggagcctg ggcccaaaca gcagcttccg      60
gagtcggaag gagctgagga agaagacaga ctgaaggagc ttgcgacttt tccgcctcgg     120
caaccggacc cagcagcaag caggacgggc ggcgctctgc tactggtccc gttaagccag     180
agtagcccaa gccctgaagt cactgctcat ccggaatgga aatcccgccg accaactacc     240
cagcctccag ggcggccttg gtggcacaga actacatcaa ctaccagcag gggaccccgc     300
acagggtgtt tgaggtgcag aaggtcaaac aagccagcat ggaggatatt ccaggaagag     360
gacataagta tcgcccttaaa tttgctgttg aagaaattat acaaaaacaa gttaaggtga     420
actgcacagc tgaagtactt tacccttcaa cgggacaaga aactgcacca gaagtcaact     480
tcacatttga aggagaaact ggaagaatc cagatgaaga agacaacaca ttttatcaaa     540
gacttaagtc catgaaggaa ccgctagaag cacaaaatat tccagacaat tttggaaatg     600
tatctccaga aatgacgctc gttctacatt tagcctgggt tgcctgtggt tatataatat     660
ggcaaaattc tactgaagac acatggtata aaatggtaaa aattcaaact gtcaagcaag     720
tgcaaagaaa tgatgacttt attgaattag actacaccat tctacttcat aatatagcat     780
ctcaggagat tattccctgg caaatgcaag ttctctggca tccacaatac ggcactaaag     840
taaaacataa tagccgtctg ccaaaggaag tacaactgga ataaacaaaa accctaacac     900
tggaagtgta aacatgtcta ttgatgtgta tgccaatttc actggcatct agcttatgag     960
gccaaataat cccaaagtgt cactttatat aaatgtcttg attacagtat agaactttat    1020
agagtccata atacaaagta tcactacata aaaatgtctt taaaacagta atagtggtat    1080
gtatatccaa aataaaaagc ttcaatttca gcc                                   1113

<210> SEQ ID NO 2
<211> LENGTH: 222
<212> TYPE: PRT
```

```
<213> ORGANISM: human

<400> SEQUENCE: 2

Met Glu Ile Pro Pro Thr Asn Tyr Pro Ala Ser Arg Ala Ala Leu Val
1               5                   10                  15

Ala Gln Asn Tyr Ile Asn Tyr Gln Gln Gly Thr Pro His Arg Val Phe
            20                  25                  30

Glu Val Gln Lys Val Lys Gln Ala Ser Met Glu Asp Ile Pro Gly Arg
            35                  40                  45

Gly His Lys Tyr Arg Leu Lys Phe Ala Val Glu Glu Ile Ile Gln Lys
            50                  55                  60

Gln Val Lys Val Asn Cys Thr Ala Glu Val Leu Tyr Pro Ser Thr Gly
65                      70                  75                  80

Gln Glu Thr Ala Pro Glu Val Asn Phe Thr Phe Glu Gly Glu Thr Gly
                85                  90                  95

Lys Asn Pro Asp Glu Glu Asp Asn Thr Phe Tyr Gln Arg Leu Lys Ser
            100                 105                 110

Met Lys Glu Pro Leu Glu Ala Gln Asn Ile Pro Asp Asn Phe Gly Asn
            115                 120                 125

Val Ser Pro Glu Met Thr Leu Val Leu His Leu Ala Trp Val Ala Cys
        130                 135                 140

Gly Tyr Ile Ile Trp Gln Asn Ser Thr Glu Asp Thr Trp Tyr Lys Met
145                 150                 155                 160

Val Lys Ile Gln Thr Val Lys Gln Val Gln Arg Asn Asp Asp Phe Ile
                165                 170                 175

Glu Leu Asp Tyr Thr Ile Leu Leu His Asn Ile Ala Ser Gln Glu Ile
            180                 185                 190

Ile Pro Trp Gln Met Gln Val Leu Trp His Pro Gln Tyr Gly Thr Lys
            195                 200                 205

Val Lys His Asn Ser Arg Leu Pro Lys Glu Val Gln Leu Glu
            210                 215                 220
```